United States Patent
Tsuji et al.

(10) Patent No.: US 7,820,197 B2
(45) Date of Patent: Oct. 26, 2010

(54) PERCUTANEOUS PREPARATIONS

(75) Inventors: Yasuhiro Tsuji, Kanonji (JP); Kei Tamura, Toyama (JP); Yuuhiro Yamazaki, Imizu-gun (JP); Yoshihiro Sawai, Imizu-gun (JP)

(73) Assignee: Astellas Pharma Inc., Tokyo (JP)

( * ) Notice: Subject to any disclaimer, the term of this patent is extended or adjusted under 35 U.S.C. 154(b) by 1247 days.

(21) Appl. No.: 10/502,951

(22) PCT Filed: Feb. 13, 2003

(86) PCT No.: PCT/JP03/01502

§ 371 (c)(1),
(2), (4) Date: Jul. 29, 2004

(87) PCT Pub. No.: WO03/068241

PCT Pub. Date: Aug. 21, 2003

(65) Prior Publication Data
US 2005/0106186 A1 May 19, 2005

(30) Foreign Application Priority Data
Feb. 14, 2002 (JP) ............... 2002-037405
Dec. 27, 2002 (JP) ............... 2002-381318

(51) Int. Cl.
*A61F 13/00* (2006.01)
*A61K 31/66* (2006.01)

(52) U.S. Cl. .............. 424/449; 424/443; 424/447; 514/108

(58) Field of Classification Search ............... 424/447, 424/449
See application file for complete search history.

(56) References Cited

U.S. PATENT DOCUMENTS

| | | | |
|---|---|---|---|
| 5,133,972 A | 7/1992 | Ferrini et al. | |
| 5,958,908 A | 9/1999 | Dohi et al. | |
| 6,008,206 A | 12/1999 | Dohi et al. | |
| 6,638,920 B2 * | 10/2003 | Thompson | 514/108 |
| 6,896,898 B1 * | 5/2005 | Xiong et al. | 424/449 |

FOREIGN PATENT DOCUMENTS

| | | |
|---|---|---|
| EP | 0 407 344 A2 | 1/1991 |
| EP | 0407344 | 1/1991 |
| EP | 0 600 834 A1 | 6/1994 |
| GB | 1582694 | 1/1981 |
| JP | 01-308290 | 12/1989 |
| JP | 6-99457 | 12/1994 |
| JP | 08-92101 | 4/1996 |
| JP | 08-092101 | 4/1996 |
| WO | 99/18972 | 4/1999 |
| WO | WO 00/45795 | 8/2000 |

OTHER PUBLICATIONS

Priborsky et al. Comparison of penetration enhancing ability of laurocaproam N-methyl-2-pyrrolidone and dodecyl-L-pyroglutamate. Pharmceutisch Weekblad Scientific edition. 1988, vol. 10, pp. 189-192.*
H. Fleisch, "Bisphosphonates in Bone Disease", Jul. 30, 1996, pp. 25-61, including literal translation.
EP 03 70 5125 European Search Report received Jun. 25, 2008.
Mar. 3, 2006, Office Action in Chinese application No. 03804039.5 (with translation).
Yamazaki experimental report filed in Chines application No. 03804039.5 (with translation), Jun. 2005.
Wikipedia entry for "paraffin", available at en.wikipedia.org/wiki/Paraffin, last visited Jul. 18, 2008.

* cited by examiner

*Primary Examiner*—Lakshmi S Channavajjala
(74) *Attorney, Agent, or Firm*—Finnegan, Henderson, Farabow, Garrett & Dunner LLP

(57) ABSTRACT

A bisphosphonic acid derivative-containing percutaneous preparation of an excellent percutaneous permeability, comprising a bisphosphonic acid derivative such as incadronic acid, minodronic acid, etc., or pharmaceutically acceptable salts thereof, a solubilizing agent for the derivative or pharmaceutically acceptable salts thereof, and an amphiphilic solubilizing auxiliary agent, which may optionally contain a suspension-type base such as a polyvalent alcohol, a higher fatty acid ester, a liquid hydrocarbon or a vegetable oil, etc. This preparation has an excellent percutaneous permeability, reduces burdens on the patient, does not deteriorate the patient's compliance even in the administration over a prolonged period of time and can achieve the therapeutic effects in a short period of time.

3 Claims, No Drawings

PERCUTANEOUS PREPARATIONS

TECHNICAL FIELD

The present invention relates to bisphosphonic acid derivative-containing percutaneous preparations having an excellent percutaneous permeability, which comprises bisphosphonic acid derivatives or pharmaceutically acceptable salts thereof, and solvents for the bisphosphonic acid derivatives or pharmaceutically acceptable salts thereof and amphiphilic solubilizing auxiliary agents. More particularly, the present invention relates to percutaneous preparations comprising incadronic acid or minodronic acid, or pharmaceutically acceptable salts thereof.

BACKGROUND ART

Certain synthetic bisphosphonate compounds having a methanebisphosphonic acid structure which are structurally analogous to pyrophosphoric acid and stable also in vivo (hereinafter referred to as bisphosphonic acid derivatives or pharmaceutically acceptable salts thereof, or sometimes merely as bisphosphonic acid derivatives) have biological actions such as an excellent bone resorption inhibitory action, ectopic calcification inhibitory action, etc. and are useful as agents for the treatment of diseases associated with accelerated bone resorption, ectopic calcification, etc., e.g., osteoporosis, Paget's disease of bone, hypercalcemia accompanied by malignant tumor, etc. Some of them have already been used clinically.

As bisphosphonates commercially available so far and currently under development, there are known alendronate, ibandronate, incadronate, etidronate, olpadronate, clodronate, zoledronate, tiludronate, neridronate, pamidronate, risendronate, minodronic acid [1-hydroxy-2-(imidazo[1,2-a]pyridin-3-yl)ethylidenebisphosphonic acid], disodium 1-hydroxy-3-(1-pyrrolidinyl)propylidenebisphosphonate, etc.

In particular, incadronic acid or minodronic acid or pharmaceutically acceptable salts thereof including incadronate (disodium incadronate) or minodronic acid have a potent bone resorption inhibitory action, an excellent anti-inflammatory action and antipyretic analgesic action, and are useful for diseases such as hypercalcemia, etc., caused by bone resorption (JP-B-6-99457 and JP-B-7-629).

Pharmacokinetic studies on tiludronate, pamidronate, etidronate, clodronate and alendronate have been extensively made. It is reported that these bisphosphonates are poor in bioavailability when orally administered, should avoid alimentary effects since their absorption is suppressed especially in the presence of calcium or iron, deposit very rapidly onto bone and might cause gastrointestinal disorders by oral administration though they are mild, and further that recent studies revealed bioavailability of the bisphosphonates even when administered pernasally or percutaneously, and so on (see "Bisphosphonates and Bone Disease: Kiso-to-Rinsho (The Clinical Report)" Jul. 30, 1996, published by Ishiyaku Publishers Inc.).

On the other hand, British Patent No. 1,582,694 discloses a composition suitable particularly for topically treating the anomalous mobilization and deposition of calcium phosphate salts in the tissues of humans and lower animals, including percutaneous administration, which comprises a safe and effective amount of an organophosphonate compound in combination with a carrier containing a safe and effective amount of an organosulfoxide compound as a specific penetration enhancer. Particularly in the patent supra, a composition composed of etidronate or clodronate, decyl methyl sulfoxide, water, or a cream base penetrating carrier composed of water, ethanol, stearyl alcohol and lanolin is shown as a specific example of formulations. It is described in the patent that a typical organosulfoxide compound, decyl methyl sulfoxide, enhanced especially in the skin permeation test in vitro by about 6-fold the penetration effect of etidronate, which is a typical example of the organophosphonates, as compared to control; in the in vivo tests with rats to verify therapeutic effects on dihydrotachysterol-induced calcification (calciphylaxis), a skin calcium level (%) was 0.035 in the normal control and 0.067 in the control with etidronate alone dissolved in the penetrating carrier vehicle, whereas the skin calcium level was enhanced to 2.026 when treated with a composition composed of etidronate and a penetrating carrier containing decyl methyl sulfoxide.

U.S. Pat. No. 5,133,972 also discloses a pharmaceutical preparation for topical application, which comprises a particular methanediphosphonic acid represented by formula (I) below:

(wherein ... Het1 is unsubstituted or substituted, monocyclic, 5- or 6-membered monoaza-, diaza- or thiaza-aryl that is bonded via a ring carbon atom, or $R_1$ is ... hydroxy group, $R_2$ is -A-$R_3$, in which A is an alkylene group and, on the one hand, $R_3$ is Het2, which is Het1 bonded via a ring carbon or ring nitrogen atom, or, ... ) (As to further detailed definitions, please see the above-mentioned U.S. Patent specification) or pharmaceutically acceptable salts thereof. According to the above-mentioned Specification, it is described that "it was discovered that pharmaceutically acceptable methanebisphosphonic acids, especially those of formula I below, are readily conveyed through the skin and can thus immediately act systemically," indicating that these unexpected discoveries were made during the particular studies in vitro. Though the test method is described in detail, any data concerning percutaneous permeability is not disclosed at all. The above-mentioned Specification merely describes various formulations of zoledronate specifically.

Incadronic acid, the chemical structure of which is characterized in binding its cycloheptane ring at the 1-position not via a lower alkylene group, or pharmaceutically acceptable salts thereof and the said minodronic acid, the chemical structure of which is characterized in having the imidazopyridine ring which is not a monocyclic hetero-ring but a bicyclic hetero-ring, or pharmaceutically acceptable salts thereof are not included in the chemical formula I described in the U.S. patent.

Thus, any specific percutaneous preparation which contains as the effective ingredient incadronic acid or minodronic acid, or pharmaceutically acceptable salts thereof is unknown so far.

In these bisphosphonates, pamidronate or the like is made available as an oral preparation. However, the bisphosphonates are poor in absorbability per os and sometimes cause an undesired effect such as gastrointestinal disorders, etc. when a large dose is administered. In practice, the bisphosphonates are administered as injections. In the form of injections, pain is attendant and patients' compliance is lowered where prolonged administration is required. Especially, a bisphosphonate having a weak effect is often administered continuously over a prolonged period of time. Under these situations, a great demand still exists to develop a preparation with a minimized burden on the patient without deteriorating patients' compliance even when administered over a long period of time. It is also earnestly desired to develop a preparation capable of achieving therapeutic effects in a short period of time.

DISCLOSURE OF THE INVENTION

Under such a technical level, the present inventors made extensive studies to develop pharmaceutical preparations of incadronate, which is called the bisphosphonate of the third generation, without relying on oral administration, injections such as intravenous drip infusion, etc. As a result, it has been found that incadronate shows an excellent percutaneous permeability and targeting toward bone tissues and at the same time, excellent drug retention in bone tissues which was unexpected from conventional findings on the bisphosphonates.

The present inventors further performed similar tests also on minodronic acid and unexpectedly found that minodronic acid shows the same effect as in incadronate, although minodronic acid is a compound having properties that is practically insoluble in water unlike incadronate, insoluble even in an organic solvent and soluble in an alkaline solvent. Based on the finding, it has been attained for the first time to provide percutaneous preparations comprising as the effective ingredient incadronic acid or minodronic acid, or pharmaceutically acceptable salts thereof.

The present inventors made further investigations on these bisphosphonates to optimize percutaneous absorption preparations and found that extremely high percutaneous permeability is shown in the system where a suspension-type base is used.

The present inventors made further extensive studies to clarify causes for high permeability when using the suspension-type base. As a result, it has been demonstrated that when an amphiphilic solubilizing auxiliary agent soluble in both water and oil is formulated in the percutaneous drug system, a more excellent percutaneous permeability is exhibited than the preparations formulated with decyl methyl sulfoxide described in the British Patent No. 1,582,694 supra and known to promote a particularly excellent percutaneous permeability, and the formulation containing this amphiphilic solubilizing auxiliary agent shows effects not only on the bisphosphonates such as incadronate or minodronic acid but also on the other bisphosphonates in a similar fashion.

It has also been demonstrated that the percutaneous preparation of minodronic acid formulated with the amphiphilic solubilizing auxiliary agent shows a percutaneous permeability enhanced by several-fold, when compared to a similar percutaneous preparation of alendronate. As such, it is an unexpectedly marked effect in the art to differ in the percutaneous permeability by several times between the preparations of the same preparation materials except for the effective ingredient and among the bisphosphonates, minodronic acid, etc. were recognized to be particularly useful in providing excellent percutaneous preparations.

The present invention has been accomplished based on these findings and relates to:

(1) a bisphosphonic acid derivative-containing percutaneous preparation having an excellent percutaneous absorption, which comprises a bisphosphonic acid derivative or a pharmaceutically acceptable salt thereof, a solubilizing agent for the bisphosphonic acid derivative or a pharmaceutically acceptable salt thereof, and an amphiphilic solubilizing auxiliary agent;

(2) the percutaneous preparation according to (1), wherein a percutaneously effective dose of the bisphosphonic acid derivative or a pharmaceutically acceptable salt thereof, and 0.01 to 10 parts by weight of the solubilizing agent for the bisphosphonic acid derivative or a pharmaceutically acceptable salt thereof based on 1 part by weight of the bisphosphonic acid derivative or a pharmaceutically acceptable salt thereof and 1 to 10 parts by weight of the amphiphilic solubilizing auxiliary agent based on the whole preparation are formulated;

(3) the percutaneous preparation according to (1) or (2), which contains a suspension-type base;

(4) the percutaneous preparation according to (3), wherein the suspension-type base is a polyvalent alcohol, a higher fatty acid ester, a liquid hydrocarbon or a vegetable oil;

(5) the percutaneous preparation according to (4), wherein a compounding amount of the suspension-type base is 0.01 to 50 wt % based on the whole preparation;

(6) the percutaneous preparation according to any one of (1) through (5), wherein the bisphosphonic acid derivative or a pharmaceutically acceptable salt thereof is at least one selected from the group consisting of alendronic acid, ibandronic acid, incadronic acid, etidronic acid, olpadronic acid, clodronic acid, zoledronic acid, tiludronic acid, neridronic acid, pamidronic acid, risendronic acid, minodronic acid and 1-hydroxy-3-(1-pyrrolidinyl)propylidenebisphosphonic acid as well as pharmaceutically acceptable salts thereof;

(7) the percutaneous preparation according to (6), wherein the bisphosphonic acid derivative or a pharmaceutically acceptable salt thereof is incadronate or minodronic acid;

(8) the percutaneous preparation according to (7), wherein the solubilizing agent for the bisphosphonic acid derivative or a pharmaceutically acceptable salt thereof is water or alkaline water;

(9) the percutaneous preparation according to any one of (1) through (8), wherein the amphiphilic solubilizing auxiliary agent is a glycerine fatty acid ester, a polyglycerine fatty acid ester, a sorbitan fatty acid ester, a polyoxyethylene sorbitan fatty acid ester, a polyoxyethylene sorbitol fatty acid ester, a polyoxyethylene alkyl-formaldehyde adduct, a polyoxyethylene sterol/hydrogenated sterol, a polyethylene glycol fatty acid ester, a polyoxyethylene alkyl ether, a polyoxyethylene polyoxypropylene alkyl ether, a polyoxyethylene polyoxypropylene glycol, a polyoxyethylene alkyl phenyl ether, a yellow beeswax derivative, a polyoxyethylene alkylamine/fatty acid amide, a polyoxyethylene alkyl ether phosphoric acid/phosphate, a monofatty acid polyoxyethylene-hydrogenated castor oil, N-methyl-2-pyrrolidone, acetone, methyl ethyl ketone, methyl isobutyl ketone, triethyl citrate, ethyl acetate, ethyl lactate, triacetine, pantothenyl ethyl ether, ethylene glycol monobutyl ether, dimethyl ether, isopropanolamine, diisopropanolamine, 2-amino-2-methyl-1-propanol, 2-amino-2-methyl-1-propanediol, N,N-dimethylacetamide, geraniol denatured alcohol, sucrose octaacetate denatured alcohol, linalyl acetate denatured alcohol, benzyl alcohol, butanol, 2-butanol, diethylene glycol, dipropylene glycol, 1,3-butylene glycol, propylene glycol, propylene carbonate, thioglycolic acid, propionic acid, methanesulfonic acid, glacial acetic acid, lactic acid, butyric acid or ichthammol;

(10) the percutaneous preparation according to any one of (1) through (9), wherein a ratio of a soluble form to an insoluble form of the bisphosphonic acid derivative or a pharmaceutically acceptable salt thereof contained in the preparation is 1:0.01 to 1:0.9; and,

(11) the percutaneous preparation according to any one of (1) through (10), wherein a liquid property of the solute of bisphosphonic acid and the solubilizing agent is adjusted to the pH of 4 to 7.

The present invention further relates to:

(12) a percutaneous preparation comprising incadronic acid or minodronic acid, or a pharmaceutically acceptable salt thereof;

(13) the percutaneous preparation according to (12), which contains a suspension-type base;

(14) the percutaneous preparation according to (13), wherein the suspension-type base is a polyvalent alcohol, a higher fatty acid ester, a liquid hydrocarbon or a vegetable oil;

(15) the percutaneous preparation according to (14), wherein a compounding amount of the suspension-type base is 0.01 to 50 wt % based on the whole preparation;

(16) the percutaneous preparation according to any one of (12) to (15), wherein the preparation is in the form of a plaster formulation, an ointment, a gel, an emulsion, a lotion or a liquid;

(17) the percutaneous preparation according to (16), wherein the form of the preparation is a plaster formulation; and,

(18) the percutaneous preparation according to (17), wherein the form of the preparation is a tape.

BEST MODE FOR CARRYING OUT THE INVENTION

Hereinafter the percutaneous preparation of the present invention is described in detail.

The "percutaneous preparation" of the present invention is intended to mean a percutaneous preparation comprising incadronic acid or minodronic acid, or a pharmaceutically acceptable salt thereof, and a percutaneous preparation comprising at least the bisphosphonic acid derivative or a pharmaceutically acceptable salt thereof, the solubilizing agent for the bisphosphonic acid derivative or a pharmaceutically acceptable salt thereof and the amphiphilic solubilizing auxiliary agent.

The percutaneous preparation of the present invention comprising incadronic acid or minodronic acid or a pharmaceutically acceptable salt thereof (hereinafter sometimes merely referred to as "the percutaneous preparation comprising minodronic acid, etc.") is composed of incadronic acid or minodronic acid or a pharmaceutically acceptable salt thereof, and a base for percutaneous administration. Particularly preferred is the percutaneous preparation which contains the suspension-type base as one component of the base for percutaneous administration. The percutaneous preparation of the present invention containing minodronic acid, etc. is characterized by an excellent percutaneous permeability, targeting to the bone tissues and drug retention and further characterized in that significant percutaneous permeability is exhibited especially in the presence of the suspension-type base. Thus, the invention is useful as developing a new type of route for administration of minodronic acid, etc.

The pharmaceutically acceptable salts of incadronic acid, which is one of the effective ingredients in the percutaneous preparation of the present invention comprising incadronic acid or minodronic acid, or pharmaceutically acceptable salts thereof, are not particularly limited so long as they are pharmaceutically acceptable salts that can attain the objects of the present invention. However, disodium incadronate (hereinafter the disodium salt is referred to as incadronate) is especially preferable. Turning to minodronic acid, it can be converted into the salt but is normally used in its free form.

The percutaneous preparation of the present invention containing minodronic acid, etc. does not prohibit compounding 2 or more of incadronic acid, minodronic acid, or pharmaceutically acceptable salts thereof to prepare the percutaneous preparation, or using in combination with other bisphosphonic acid derivatives or pharmaceutically acceptable salts thereof to prepare the percutaneous preparation as the combined drug. Herein, what is meant by the other "bisphosphonates" will be explained later.

The compounding amount of minodronic acid, etc. as the effective ingredients may be an effective dose pharmacologically required for the percutaneous preparation. Especially the compounding amount of the effective ingredient is somewhat different between incadronic acid or pharmaceutically acceptable salts thereof and minodronic acid or pharmaceutically acceptable salts thereof, and may also vary depending on the forms of the percutaneous preparation, bases for percutaneous administration used in the percutaneous preparation, their compounding amounts, etc. Therefore, the compounding amount cannot be determined in general but roughly speaking, is suitably in the range of 0.01 to 10 wt % and particularly preferably from 0.1 to 5 wt %, based on the whole preparation. Where 2 or more effective ingredients are employed, it is preferred that the combined amounts of these ingredients are within the range for formulation described above.

The "suspension-type base," which is one of the bases for percutaneous administration used in the percutaneous preparation of the present invention containing minodronic acid, etc. is not particularly limited, as long as it is a medicament that can significantly enhance the percutaneous permeability when the skin permeation test is carried out using a solution of the effective ingredients of the present invention and is a suspension-type base capable of suspending the effective ingredients of the present invention. Specifically, preferred suspension-type bases include, for example, polyvalent alcohols such as ethylene glycol, propylene glycol, butanediol, triethylene glycol, polyethylene glycol, glycerine, etc.; higher fatty acid esters having at least 12 carbon atoms, such as hexyl laurate, butyl stearate, isopropyl palmitate, isopropyl myristate, octyldodecyl myristate, myristyl myristate, etc.; liquid hydrocarbons such as liquid paraffin, etc.; or various vegetable oils such as soybean oil, sesame oil, corn oil, linseed oil, sunflower oil, cotton seed oil, olive oil, castor oil, peanut oil, etc. These suspension-type bases exert the functions also as softening agents when formulated as the components for a plaster formulation, etc.

The compounding amount of the suspension-type base may vary depending upon the preparation form of percutaneous preparation, bases for percutaneous administration used for the percutaneous preparation and their compounding amounts, solubility of drugs, etc. and cannot be determined in general. Roughly, the compounding amount is suitably 0.01 to 50 wt % and preferably 0.1 to 40 wt %, based on the whole preparation. When formulated as components in a plaster formulation, etc., these suspension-type bases also exhibit the function as softeners.

In the percutaneous preparation of the present invention containing minodronic acid, etc., it has been demonstrated that only by incorporating the amphiphilic solubilizing auxiliary agent later described especially without adding any percutaneous permeation promoter, the preparation shows an excellent percutaneous permeability as compared to organo-sulfoxide compound-containing percutaneous preparations hitherto known to promote the excellent percutaneous permeability. In the percutaneous preparation of the present invention, it has also been demonstrated that the system added with a permeation promoter such as urea, etc. significantly enhances percutaneous permeability in the bisphosphonate-containing percutaneous system, as compared to the system added with no promoter. Therefore, percutaneous permeation enhancers capable of enhancing the percutaneous permeability of bisphosphonates can additionally be formulated in the percutaneous preparation of the present invention, in such a range that does not impair the objects of the present invention.

Examples of such percutaneous permeation enhancers include terpenes such as peppermint oil, orange oil, turpentine oil, l-menthol, etc. and natural essential oil containing the terpenes, dibasic acid diesters such as diethyl sebacate, diisopropyl adipate, etc., which are disclosed in the above-mentioned JP-A-5-201879, ethanol and urea, or decyl methyl sulfoxide described in the above-mentioned British Patent Specification No. 1,582,694, and the like. Disclosures described in these official gazettes concerning percutaneous permeation enhancers are hereby incorporated by reference in the specification.

The percutaneous preparation of the present invention containing minodronic acid, etc. shows a good percutaneous permeability especially in the acidic region. From a viewpoint of avoiding skin irritation of the percutaneous preparation, the preparation is adjusted to be weakly acidic to neutral, preferably weakly acidic, in the region in contact with the skin applied. It is thus preferred to add a buffer to a solution composed of the bisphosphonic acid derivative or its pharmaceutically acceptable salt to adjust the pH to 4-7 and formulate the solution in a base for the percutaneous preparation.

Accordingly, where incadronic acid or its pharmaceutically acceptable salts are used as the effective ingredients and since these effective ingredients are water-soluble, it is preferred to add a buffer to the aqueous solution to adjust the pH to approximately 4 to 7 and formulate the aqueous solution in a base for the percutaneous preparation, especially in a suspension-type base or other base for the percutaneous preparation. On the other hand, in the case of the percutaneous preparation containing minodronic acid as the effective ingredient, minodronic acid is previously dissolved in an alkaline solvent and the solution is neutralized with an acidic solvent to prepare the solution of minodronic acid. Though minodronic acid is not water-soluble, it has revealed that even when neutralized, minodronic acid does not precipitate as a solid drug but maintains its aqueous solution state and exhibits an excellent percutaneous permeability in the state. Therefore, in making the minodronic acid-containing percutaneous preparation in accordance with the present invention, it is preferred to prepare a neutralized solution of minodronic acid (pH of about 4 to 7) and formulate the solution in a base for percutaneous administration, especially in a suspension-type base or other bases for percutaneous administration to adjust the liquid property.

The buffer used herein may be any buffer so long as it is a pharmaceutically acceptable buffer and specific examples include organic acids such as citric acid, tartaric acid, succinic acid, malic acid, maleic acid, acetic acid, etc., salts of these organic acids, primary, secondary or tertiary phosphate (e.g., sodium primary phosphate, sodium secondary phosphate, etc.), amino acids such as glycine, etc. or salts of the amino acids, etc., or a mixture thereof. The organic acids described above also have the properties that are particularly useful in formulating in a plaster formulation using a high molecular base.

As described above, the percutaneous preparation of the present invention containing minodronic acid, etc. is characterized by its excellent percutaneous permeability, targeting to bone tissues and drug retention, and exhibits a significant percutaneous permeability especially in the presence of the suspension-type base. Thus, the "percutaneous preparation" in the percutaneous preparation of the present invention containing minodronic acid, etc. may be any type of percutaneous preparation so long as the preparation is a type that can achieve these effects. In particular, the preparation may be all types of external preparations that can achieve the effects of the present invention, including a plaster formulation such as a plaster preparation, a tape preparation, etc., an ointment such as an oil base ointment using white petrolatum as a base, a hydrophilic ointment using polyethylene glycol as a base, etc., a gel using carboxyvinyl polymer (Carbopol) as a base (also termed a hydrogel or hydrophilic gel ointment), an emulsion using water, oily components and an emulsifying agent as bases (also termed a cream), a lotion, and the like. Particularly preferred are the types of preparation suitable for containing the suspension-type base, for example, the types of preparation such as the plaster formulation, ointment, gel, emulsion, lotion, etc. described above. Among other things, the plaster formulation such as a plaster preparation, a tape preparation, etc., especially a tape preparation is preferred. These percutaneous preparations can be prepared by applying the procedures for making preparations used in the fields of pharmaceutical preparations and cosmetics.

As a typical example of the percutaneous preparation of the present invention, a plaster formulation is illustratively explained below. Other external preparations can be prepared in a conventional manner as will be later described in EXAMPLES, and this illustration is not intended to limit the type of preparation in any way.

The plaster formulation is composed of a support (backing), an adhesive mass having a pressure-sensitive adhesion which is capable of releasing drugs, and a releasable film for protecting the adhesive mass layer.

In the adhesive mass layer, the effective ingredient minodronic acid, etc. and bases for plaster formulation are formulated. It is particularly preferred to formulate the suspension-type base as one of the bases for plaster formulation.

Specific examples of adhesive components used in the base for plaster formulation are:

(1) natural rubber or synthetic rubber including natural rubber, styrene-butadiene rubber (SBR), polyisoprene rubber, polyisobutylene rubber, styrene-isoprene-styrene block copolymer (SIS), styrene-butadiene-styrene block copolymer (SBS), silicone rubber, or acrylic copolymers (also termed acrylic resins) such as (meth)acrylic acid-(meth)acrylate copolymers, etc.;

(2) highly water-absorbing high molecular substances such as acrylic acid-starch, etc.; or, (3) hydrophilic high molecular substances such as polyacrylic acid, sodium polyacrylate, carboxymethyl cellulose (CMC), carboxymethyl cellulose sodium salt (CMCNa), polyvinyl alcohol (PVA), polyvinyl pyrrolidone (PVP), methyl vinyl ether-maleic anhydride copolymer, sodium alginate, propylene glycol alginate, pectin, xanthan gum, locust bean gum, guar gum, arabiano-galactan, sodium hyaluronate, etc.; and the like. Rubbers or the like may be used as latex emulsions.

These adhesive components can be formulated solely or in an appropriate combination of 2 or more. The compounding amount of the adhesive component may vary depending upon difference in plaster preparation or tape preparation, kind of effective ingredients, or kind and amount of suspension-type base or other additives formulated, and it is difficult to determine the compounding amount in general. However, it is generally preferred to formulate the adhesive component in approximately 20 to 99 wt %, especially about 30 to about 98.5 wt %, based on the whole (in this case, the adhesive mass).

As the other additives, there are sludging agents such as gelatin; powdery excipients such as kaolin, bentonite, zinc oxide, etc.; tackifying agents such as petroleum resins, e.g., Quintone (trade name, manufactured by Zeon Corp., aliphatic hydrocarbon resin), Arkon (trade name, manufactured by Arakawa Chemical, Inc.; aliphatic hydrocarbon resin), etc., rosin, hydrogenated rosin, ester gum, terpene resin, etc.; softeners such as polybutene, etc. (polybutene has an adhesive property by itself and behaves also as a tackifying agent but is listed as one of softeners, since it has an action of softening rubber components without adding any other softening agent); surfactants such as polyoxyethylene-hydrogenated castor oil [e.g., Cremophor (registered trademark) RH40 (manufactured by BASF), HCO-40, HCO-60, etc. (manufactured by Nikko Chemicals, Inc.)], polyoxyethylene sorbitan higher fatty acid esters [e.g., Tween 80 (manufactured by Kanto Kagaku), etc.], sorbitan fatty acid esters, etc.; antiseptics or antioxidants (antiaging agents) such as parabens, e.g., methyl paraben, etc., sorbic acid and salts thereof, butylhydroxyanisole (BHA), dibutylhydroxytoluene (BHT), nordihydroguaiaretic acid, guaiacol esters, etc.; astringent agents such as aluminum chloride, alum, trivalent metal ion-forming salts such as aluminum alantoinate, etc.; moisturizing agents such as alkaline earth metal salts, etc.; flavoring agents; solvents (organic solvents such as ethyl acetate, etc., water, aqueous ethanol, etc.); and the like.

These other additives can be compounded singly or by appropriately selecting 2 or more, taking into account adhesive components used.

The compounding amount of these other additives may also vary depending upon difference in plaster preparation or tape preparation, kind of effective ingredients, or kind and amount of suspension-type base or other additives formulated, and it is difficult to determine the amount in general. Generally it is preferred to formulate the additives in approximately 20 to 99 wt %, especially about 30 to about 98.5 wt %, based on the whole (in this case, the adhesive mass).

To prepare the plaster formulation of the present invention containing minodronic acid, etc., a solution of the effective ingredients is prepared; the liquid property of this solution is adjusted to the pH of 4 to 7, if necessary; the adhesive component, the suspension-type base and other bases for plaster formulation are added thereto; the resultant is uniformly blended and kneaded; the kneaded product is spread onto a backing and, if necessary, dried; a releasable film is laminated thereon; and the laminate is cut into an adequate size followed by packaging. These steps are performed by applying those ordinarily used in the field of plaster formulation. In order to make the preparation of a uniform adhesive mass easy, for example, it is possible to appropriately set the order of adding or kneading the effective ingredients, suspension-type base, percutaneous permeation enhancers, buffers, adhesive components and other bases for plaster formulation, or it is also possible to perform treatments like warming, ultrasonication, etc. Spreading is performed in a conventional manner such as, by uniformly applying the kneaded adhesive mass onto a backing or a releasable film in a given thickness. Drying is performed in preparing, e.g., a tape preparation with a less moisture content, where the solvent and/or water is vaporized off. However, the solvent such as water remains in the tape preparation even after drying. As the backing, there are used cloth, unwoven fabric, plastic films, etc., with particular preference being plastic films. As the releasable film, there are advantageously employed release-treated cellophane or plastic films such as polyethylene film, etc.

It has been demonstrated that the percutaneous preparation of the present invention containing minodronic acid, etc. as the effective ingredient shows a significant percutaneous permeability, especially in the form of W/O emulsion. When an aqueous solution of incadronic acid salts, etc., and an emulsion or lotion composed of oily components and emulsifiers are prepared into the percutaneous preparation, the form of W/O emulsion is preferred. Examples of the emulsifiers used in this case include glycerine fatty acid ester, sorbitan fatty acid ester, propylene glycol fatty acid ester, polyglycerine fatty acid ester, polyoxyethylene glycerine fatty acid ester, polyoxyethylene sorbitan fatty acid ester, polyoxyethylene sorbitol fatty acid ester, polyoxyethylene alkyl ether, polyoxyethylene glycol fatty acid ester, polyoxyethylene castor oil, and polyoxyethylene-hydrogenated castor oil, etc. It is preferred to control the emulsion to the HLB of generally from 1 to 8 with these emulsifiers and then provide for use.

In addition to the suspension-type base described above, the oily components further include oily components used for emulsion or lotion preparations, for example, fatty acid esters, animal and vegetable oils, hydrocarbons, fatty acids, higher alcohol silicone oil, beeswax, paraffin wax, spermaceti, etc.

On the other hand, the percutaneous preparation of the present invention comprising at least the bisphosphonic acid derivatives or pharmaceutically acceptable salts thereof, the solubilizing agent for the bisphosphonic acid derivative and the amphiphilic solubilizing auxiliary agent is characterized by formulating amphiphilic solubilizing auxiliary agent to promote the conversion of the bisphosphonic acid derivative, especially incadronic acid or minodronic acid, or pharmaceutically acceptable salts from the crystalline form (insoluble form) into the soluble form so that the excellent percutaneous permeability and expression of sustained pharmaceutical effects eventually leading to therapeutic effects at an early stage can be achieved.

In the "bisphosphonic acid derivatives or pharmaceutically acceptable salts thereof" used in these ingredients-containing percutaneous preparation of the present invention, which contains the amphiphilic solubilizing auxiliary agent, the bisphosphonic acid derivatives or pharmaceutically acceptable salts thereof other than incadronic acid or minodronic acid or pharmaceutically acceptable salts thereof can also achieve similar effects. In the technique using the amphiphilic solubilizing auxiliary agent, the effective ingredients are not limited only to incadronic acid or minodronic acid or salts thereof. Taking into account the technical idea of the present invention, it is manifest that not only the bisphosphonates hitherto known but also bisphosphonates, which will be developed in the future, are usable as the effective ingredients, so long as they can achieve the objects of the present invention.

Therefore, the "bisphosphonic acid derivatives or pharmaceutically acceptable salts thereof" referred to in the present invention embrace all bisphosphonate compounds that are synthetic bisphosphonate compounds having the methane bisphosphonic acid structure, which is structurally analogous to pyrophosphoric acid and stable also in vivo, have biological actions including a bone resorption inhibitory action, ectopic calcification inhibitory action, etc., are useful as agents for the treatment of diseases associated with accelerated bone resorption, ectopic calcification, etc., e.g., osteoporosis, Paget's disease of bone, hypercalcemia accompanied by malignant tumor, etc. and can achieve the effects of the present invention by preparing into a composition containing the amphiphilic solubilizing auxiliary agent of the present invention.

Among others, specific examples of the bisphosphonate which is particularly preferred, include at least one selected from the group consisting of alendronic acid, ibandronic acid, incadronic acid, etidronic acid, olpadronic acid, clodronic acid, zoledronic acid, tiludronic acid, neridronic acid, pamidronic acid, risendronic acid, minodronic acid and 1-hydroxy-3-(1-pyrrolidinyl)propylidenebisphosphonic acid as well as salts thereof. Particularly preferred are incadronic acid, minodronic acid or pharmaceutically acceptable salts thereof.

Also in the bisphosphonic acid-containing percutaneous preparation of the present invention, it does not hamper to make the percutaneous preparation using 2 or more effective ingredients selected from the group consisting of the bisphosphonic acid derivatives or pharmaceutically acceptable salts thereof.

The compounding amount of the bisphosphonic acid derivatives or pharmaceutically acceptable salts thereof as the effective ingredients may be an effective dose pharmacologically required for the percutaneous preparation. In particular, the compounding amount of the effective ingredient may vary depending upon kind of the effective ingredient and may also vary depending upon the kind, amount, etc. of percutaneous preparation or bases for the percutaneous preparation to be formulated, and cannot be determined in general. Roughly, the compounding amount is suitably from 0.01 to 10 wt %, preferably 0.1 to 5 wt %. Where 2 or more effective ingredients are employed, it is preferred to set the total amount within the above range of the compounding amount.

The "amphiphilic solubilizing auxiliary agent" used in the bisphosphonic acid derivative-containing percutaneous preparation of the present invention is intended to mean a substance which is soluble in both water and oil and promotes the conversion of the bisphosphonic acid derivatives from the crystalline form (insoluble form) to the soluble type. As long as it is an amphiphilic solubilizing auxiliary agent that can achieve the objects of the present invention, there is no particular restriction. Specific examples of the amphiphilic solubilizing auxiliary agents, which are particularly preferred, are glycerine fatty acid esters such as glyceryl monostearate, glyceryl monolaurate, polyoxyethylene glyceryl monostearate, polyoxyethylene glyceryl monooleate, etc.; polyglycerine fatty acid esters such as hexaglyceryl monostearate, hexaglyceryl monooleate, polyglyceryl isostearate, polyglyceryl distearate, decaglyceryl diisostearate, polyglyceryl dioleate, etc.; sorbitan fatty acid esters such as sorbitan monolaurate, etc.; polyoxyethylene sorbitan fatty acid esters such as polyoxyethylene sorbitan monostearate, polyoxyethylene sorbitan monooleate, etc.; polyoxyethylene sorbitol fatty acid esters such as polyoxyethylene sorbitol tetraoleate, etc.; polyoxyethylene alkyl-formaldehyde adducts such as polyoxyethylene nonyl-formaldehyde adduct, etc.; polyoxyethylene sterol/hydrogenated sterols such as polyoxyethylene phytosterol, etc.; polyethylene glycol fatty acid esters such as polyethylene glycol monostearate, polyethylene glycol monolaurate, polyethylene glycol monooleate, polyethylene glycol myristate, polyethylene glycol monoisostearate, polyethylene glycol distearate, polyethylene glycol diisostearate, polyethylene glycol dilaurate, polyethylene glycol dioleate, etc.; polyoxyethylene alkyl ethers such as polyoxyethylene lauryl ether, polyoxyethylene cetyl ether, polyoxyethylene stearyl ether, polyoxyethylene behenyl ether, polyoxyethylene synthetic alkyl ether, polyoxyethylene secondary alkyl ether, polyoxyethylene oleyl ether, polyoxyethylene tridecyl ether, polyoxyethylene myristyl ether, polyoxyethylene isostearyl ether, polyoxyethylene linolyl ether, polyoxyethylene capryl caproyl ether, etc.; polyoxyethylene polyoxypropylene alkyl ethers such as polyoxyethylene polyoxypropylene cetyl ether, etc.; polyoxyethylene polyoxypropylene glycols such as polyoxyethylene polyoxypropylene glycol, etc.; polyoxyethylene alkyl phenyl ethers such as polyoxyethylene nonyl phenyl ether, etc.; beeswax derivatives such as polyoxyethylene sorbitol beeswax, polyethylene glycol beeswax, etc.; polyoxyethylene alkylamine/fatty acid amides such as polyoxyethylene stearylamine, polyoxyethylene oleylamine, polyoxyethylene stearic acid amid, etc.; polyoxyethylene alkyl ether phosphoric acid/phosphates such as polyoxyethylene cetyl ether sodium phosphate, dipolyoxyethylene alkyl ether phosphoric acid, tripolyoxyethylene alkyl ether phosphoric acid, etc.; monofatty acid polyoxyethylene-hydrogenated castor oil such as lauric acid polyoxyethylene-hydrogenated castor oil, monoisostearic acid polyoxyethylene-hydrogenated castor oil, etc.; N-methyl-2-pyrrolidone; acetone; methyl ethyl ketone; methyl isobutyl ketone; triethyl citrate; ethyl acetate; ethyl lactate; triacetine; pantothenyl ethyl ether; ethylene glycol monobutyl ether; dimethyl ether; isopropanolamine; diisopropanolamine; 2-amino-2-methyl-1-propanol; 2-amino-2-methyl-1-propanediol; N,N-dimethylacetamide; geraniol denatured alcohol; sucrose octaacetate denatured alcohol; linalyl acetate denatured alcohol; benzyl alcohol; butanol; 2-butanol; diethylene glycol; dipropylene glycol; 1,3-butylene glycol; propylene glycol; propylene carbonate; thioglycolic acid; propionic acid; methanesulfonic acid; glacial acetic acid; lactic acid; butyric acid or ichthammol, etc.

Among others, preferred are glycerine fatty acid esters; polyglycerine fatty acid esters; sorbitan fatty acid esters; polyoxyethylene sorbitan fatty acid esters; polyoxyethylene sorbitol fatty acid esters; polyoxyethylene alkyl-formaldehyde adducts; polyoxyethylene sterol/hydrogenated sterols; polyethylene glycol fatty acid esters; polyoxyethylene alkyl ethers; polyoxyethylene polyoxypropylene alkyl ethers; polyoxyethylene polyoxypropylene glycols; polyoxyethylene alkyl phenyl ethers; beeswax derivatives; polyoxyethylene alkylamine/fatty acid amides; polyoxyethylene alkyl ether phosphoric acid/phosphates; monofatty acid polyoxyethylene-hydrogenated castor oil; N-methyl-2-pyrrolidone; acetone; methyl ethyl ketone; or methyl isobutyl ketone. Among them, particularly preferred are glycerine fatty acid esters; polyethylene glycol fatty acid esters; polyoxyethylene alkyl ethers; polyoxyethylene polyoxypropylene alkyl ethers; polyoxyethylene polyoxypropylene glycols; polyoxyethylene alkyl phenyl ethers; beeswax derivatives; polyoxyethylene alkylamine/fatty acid amides; polyoxyethylene alkyl ether phosphoric acid/phosphates; monofatty acid polyoxyethylene-hydrogenated castor oil; N-methyl-2-pyrrolidone; acetone; methyl ethyl ketone; or methyl isobutyl ketone.

These amphiphilic solubilizing auxiliary agents may be formulated solely, or 2 or more auxiliary agents may be appropriately selected for formulation.

The compounding amount of the amphiphilic solubilizing auxiliary agent may vary depending upon kind of the bisphosphonic acid derivative as the effective ingredient, its compounding amount, etc. and cannot be determined in general, but roughly it is preferably from 1 to 10 wt %, especially preferably from 3 to 8 wt %, based on the whole preparation.

The "solubilizing agent" used in the present invention is typically water since almost all bisphosphonates have excellent solubility in water. Where, like minodronic acid, the bisphosphonic acid derivative is not good in water solubility, a solvent for dissolving the bisphosphonic acid derivative, for example, an alkaline solvent such as an alkaline water, etc. is adopted.

The compounding amount of the solubilizing agent used may vary depending upon the kind of the bisphosphonic acid contained in the percutaneous preparation, its solubility or compounding amount per one preparation, the ratio of the soluble form to crystalline form (insoluble form) of the drugs in the percutaneous preparation, or the kind or compounding amount of amphiphilic solubilizing auxiliary agent, and cannot be determined in general. Normally it is advantageous to use 0.01 to 10 parts by weight, preferably 0.05 to 5 parts by weight of the solubilizing agent based on 1 part by weight of the bisphosphonic acid derivative, especially in view of the weight ratio of the soluble form to the crystalline form (insoluble form) of the drugs in the percutaneous preparation set to 1:0.01 to 1:0.9.

In the percutaneous preparation containing the amphiphilic solubilizing auxiliary agent of the present invention, it is preferred to regulate the weight ratio of the soluble form to the crystalline form (insoluble form) of the drug contained in the percutaneous preparation to 1:0.01 to 1:0.9, in addition to incorporation of the amphiphilic solubilizing auxiliary agent. This is especially preferred for more efficiently converting the crystalline form (insoluble form) of the drug into the soluble form by the amphiphilic solubilizing auxiliary agent and thus enhancing sustained percutaneous permeability of the drug to expect the therapeutic effects at an early stage. The ratio can be regulated by specifying the compounding ratio of the drug solution, the amphiphilic solubilizing auxiliary agent and the other bases for percutaneous administration. Particularly in order to be in the ratio described above, it is preferred that 0.01 to 10 parts by weight of the solubilizing agent is normally used based on 1 part by weight of the bisphosphonic acid derivative, and 1 to 10 parts by weight of the amphiphilic solubilizing auxiliary agent or 0.01 to 50 parts by weight of the suspension-type base chosen as the other base for percutaneous administration is used based on the whole preparation.

As described above, the "suspension-type base" used herein is not particularly limited as far as it is a suspension-type base which significantly enhances the percutaneous permeability when the skin permeation test is conducted using a solution of the bisphosphonic acid derivative. Preferred examples of the suspension-type base are suspension-type bases such as polyvalent alcohols, higher fatty acid esters having 12 carbon atoms or more, liquid hydrocarbons, vegetable oils, etc., which are given in the percutaneous preparation containing minodronic acid, etc. as the effective ingredient. These suspension-type bases may be used alone or in combination of 2 or more.

Also, the bisphosphonic acid-containing percutaneous preparation of the present invention shows a good percutaneous permeability especially in an acidic region. In view of avoiding skin irritation of the percutaneous preparation, the preparation is preferably adjusted to become weakly acidic in the region in contact with the skin applied. It is therefore preferred to add a buffer to a solution prepared by the bisphosphonic acid derivative or its pharmaceutically acceptable salt to adjust pH from about 4 to about 7 and then formulate the solution in a base for the percutaneous preparation.

The pH adjustment in the bisphosphonic acid-containing percutaneous preparation of the present invention and buffers used are the same as in the percutaneous preparation of the present invention containing minodronic acid, etc., using the same buffers.

In the bisphosphonic acid-containing percutaneous preparation of the present invention, percutaneous permeation enhancers can be added as well so that the percutaneous permeation promoting effect of the bisphosphonic acid derivative can be further improved. Accordingly, it is possible to formulate percutaneous permeation enhancers for the bisphosphonates in the percutaneous preparation of the present invention, in addition to the amphiphilic solubilizing auxiliary agent, within such a range that does not impair the objects of the invention.

As such percutaneous permeation enhancers, there are terpenes such as peppermint oil, orange oil, turpentine oil, l-menthol, etc. and natural essential oil containing the terpenes, dibasic acid diesters such as diethyl sebacate, diisopropyl adipate, etc., which are disclosed in the above-mentioned JP-A-5-201879, ethanol and urea, or decyl methyl sulfoxide described in the above-mentioned British Patent Specification No. 1,582,694, and the like. Disclosures described in these official gazettes concerning percutaneous permeation enhancers are hereby incorporated by reference in the specification.

Since the concentration of the drug contained in the preparation in a solution state or the concentration of the drug dissolved in the moisture of skin decreases accompanied by percutaneous absorption of the drug through the skin as stated above, the "percutaneous preparation" containing the amphiphilic solubilizing auxiliary agent of the present invention promotes dissolution of the drug in a crystalline state by the action of the amphiphilic solubilizing auxiliary agent and eventually exhibits an excellent percutaneous permeability.

Thus, the "percutaneous preparation" of the percutaneous preparation of the present invention containing the amphiphilic solubilizing auxiliary agent wherein the bisphosphonates are the effective ingredients may be any percutaneous preparation, so long as it takes the preparation form that can achieve the effects described above by adding the amphiphilic solubilizing auxiliary agent. As described above, the percutaneous preparation includes all types of external preparations that can achieve the effects of the present invention, including a plaster formulation, an ointment, a gel, an emulsion, a lotion, etc. These percutaneous preparations can be prepared by applying the procedures for making preparations used in the fields of pharmaceutical preparations and cosmetics.

As a typical example of the percutaneous preparation of the present invention, a plaster formulation is illustratively explained below. Other external preparations can be prepared in a conventional manner as will be later described in EXAMPLES, and this illustration is not intended to limit the type of preparation in any way.

The plaster formulation is composed of a support (backing), an adhesive mass having a pressure-sensitive adhesion which is capable of releasing drugs, and a releasable film for protecting the adhesive mass layer.

In the adhesive mass layer, a solution composed of the bisphosphonic acid derivative or its pharmaceutically acceptable salt and the solubilizing agent for the bisphosphonic acid derivative, the amphiphilic solubilizing auxiliary agent and other bases for the percutaneous preparation are formulated. It is particularly preferred to formulate the suspension-type base as one of the bases for the plaster formulation. When incadronate or minodronic acid is used as the effective ingredient, the percutaneous preparation is preferably in the form of a plaster preparation or a tape preparation, more preferably in the form of a tape preparation.

As the adhesive component used in the bases for plaster formulation, there are the natural or synthetic rubbers, highly water-absorbing high molecular substances, hydrophilic high molecular substances, etc., given as examples for the percutaneous preparation containing minodronic acid, etc. These rubbers or the like can be used as latex emulsions.

These adhesive components can be formulated solely or in an appropriate combination of 2 or more. The compounding amount of the adhesive component may vary depending upon difference in plaster preparation or tape preparation, kind of effective ingredients, or kind and amount of suspension-type base or other additives formulated, and it is difficult to determine the compounding amount in general. However, it is generally preferred to formulate the adhesive component in approximately 20 to 99 wt %, especially about 30 to about 98.5 wt %, based on the whole (in this case, the adhesive mass).

As the other additives, there are the sludging agents, softeners, surfactants, antiseptics or antioxidants, astringent agents, moisturizing agents, flavoring agents, solvents, etc., which are given as examples hereinbefore.

These other additives can be compounded singly or by appropriately selecting 2 or more, taking into account adhesive components used.

The compounding amount of these other additives may also vary depending upon difference in plaster preparation or tape preparation, kind of effective ingredients, or kind and amount of suspension-type base or other additives formulated, and it is difficult to determine the amount in general. However, it is generally preferred to formulate the additives in approximately 20 to 99 wt %, especially about 30 to about 98.5 wt %, based on the whole (in this case, the adhesive mass).

To prepare the plaster formulation of the present invention containing the bisphosphonic acid derivative; a solution is prepared using the bisphosphonic acid derivative and the solubilizing agent; the liquid property of this solution is adjusted to the pH of from 4 to 7, if necessary; the amphiphilic solubilizing auxiliary agent, the adhesive component and other bases for the plaster formulation are added thereto; the resultant is uniformly blended and kneaded; the kneaded product is spread onto a baking and, if necessary, dried; a releasable film is laminated thereon; and the laminate is cut into an adequate size followed by packaging. These steps are performed by applying those ordinarily used in the field of plaster formulation, as described above.

EXAMPLES

Hereinafter the present invention will be described in more detail by description of EXAMPLES. However, it is needless to say that the present invention is not limited to the description of these EXAMPLES.

Example 1

Ointment

After 5.0 parts of lanolin, 5.0 parts of cetostearyl alcohol and 80 parts of white petrolatum were melted on a water bath, a blend of 20% aqueous solution containing 0.5 part of incadronate, 5.0 parts of N-methyl-2-pyrrolidone and 4.5 parts of liquid paraffin was added to the molten mixture. The resultant was uniformly kneaded while warming (about 80° C.). After discontinuing warming, the resultant was made fully homogeneous to provide an ointment.

Example 2

Cream

After 5.0 parts of cetanol, 2.0 parts of stearic acid, 1.0 part of sorbitan monostearate and 1.0 part of polyoxyethylene sorbitan monostearate were melted on a water bath, a blend of 20% aqueous solution containing 1.0 part of incadronate, 5.0 parts of N-methyl-2-pyrrolidone and 9.0 parts of liquid paraffin was added to the molten mixture. The resultant was uniformly kneaded and maintained at about 75° C. A solution previously prepared by 0.1 part of methyl paraoxybenzoate and butyl paraoxybenzoate in a sufficient quantity of distilled water and warming at 80° C. was added to the kneaded mixture, followed by uniformly kneading while warming. After discontinuing warming, the resultant was made fully homogeneous to provide a cream.

Example 3

Plaster Formulation (Tape, Incadronate and N-Methyl-2-Pyrrolidone)

A blend of 20% aqueous solution containing 2.0 parts of incadronate as the effective ingredient, 5.0 parts of N-methyl-2-pyrrolidone, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 4

Plaster Formulation (Tape Preparation, Minodronic Acid and N-Methyl-2-Pyrrolidone)

A blend of 20% aqueous solution containing 2.0 parts of minodronic acid as the effective ingredient prepared using a 2-fold mol of 2M sodium hydroxide aqueous solution, 5.0 parts of N-methyl-2-pyrrolidone, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 5

Plaster Formulation (Tape Preparation, Minodronic Acid and Polyoxyethylene Lauryl Ether)

A blend of 20% aqueous solution containing 2.0 parts of minodronic acid as the effective ingredient prepared using a 2-fold mol of 2M sodium hydroxide aqueous solution, 5.0 parts of polyoxyethylene lauryl ether, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 6

Plaster Formulation (Tape Preparation, Minodronic Acid and Polyethylene Glycol Monostearate)

A blend of 20% aqueous solution containing 2.0 parts of minodronic acid as the effective ingredient prepared using a 2-fold mol of 2M sodium hydroxide aqueous solution, 5.0 parts of polyethylene glycol monostearate, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 7

Plaster Formulation (Tape Preparation, Minodronic Acid and Methyl Ethyl Ketone)

A blend of 20% aqueous solution containing 2.0 parts of minodronic acid as the effective ingredient prepared using a 2-fold mol of 2M sodium hydroxide aqueous solution, 5.0 parts of methyl ethyl ketone, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 8

Plaster Formulation (Tape Preparation, Alendronate and N-Methyl-2-Pyrrolidone)

A blend of 20% aqueous solution containing 2.0 parts of alendronate as the effective ingredient, 5.0 parts of N-methyl-2-pyrrolidone, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

Example 9

Plaster Formulation (Tape Preparation, Minodronic Acid and Methyl Isobutyl Ketone)

A blend of 20% aqueous solution containing 2.0 parts of minodronic acid as the effective ingredient prepared using a 2-fold mol of 2M sodium hydroxide aqueous solution, 5.0 parts of methyl isobutyl ketone, 2.5 parts of α-monoisostearyl glyceryl ether, 5.0 parts of isopropyl myristate and 1.0 part of sorbitan fatty acid ester was added to 40.0 parts of styrene-isoprene-styrene block copolymer, 34.5 parts of terpene resin and 10.0 parts of aliphatic hydrocarbon resin, and a sufficient quantity of ethyl acetate was added thereto. The resultant was uniformly mixed to form an adhesive mass. The adhesive mass was uniformly applied onto a releasable film followed by drying with warm air. A backing film was laminated and transferred thereon to provide a tape preparation.

The present invention is useful in terms of providing the percutaneous preparation of incadronic acid, minodronic acid or pharmaceutically acceptable salts thereof for the first time, which could not be expected especially from conventional bisphosphonate percutaneous preparations, and providing the percutaneous preparation which promotes the percutaneous permeability of bisphosphonates and has excellent sustained release by formulating the solubilizing agent for the bisphosphonates and the amphiphilic solubilizing auxiliary agent in the percutaneous bisphosphonate preparation. The percutaneous preparation of the present invention is useful since the preparation can reduce burdens on the patient with disease associated with percutaneous permeability, accelerated bone resorption, ectopic calcification, etc. and can achieve the therapeutic effects by percutaneous administration of incadronate, minodronic acid, etc. surely in a short period of time, without deteriorating the patient's compliance even when administered over a long period of time.

These effects were verified by the following examples of experiments.

Experiment 1

Percutaneous Absorption Test of $^{14}$C-Incadronate Aqueous Solution

[Test Method]

—Method of Preparing $^{14}$C-Incadronate Aqueous Solution—

That is, 5 mg of $^{14}$C-labeled incadronic acid bulk powder was weighed and 0.5N sodium hydroxide was added to become 0.069 ml, which was used as $^{14}$C-incadronate labeled product containing an amount equivalent to 6.073 mg. By adding 538.3 μl of purified water to the labeled product, an aqueous solution of 10 mg/ml of $^{14}$C-incadronate was prepared. To 200 μl of the $^{14}$C-incadronate aqueous solution, 1800 μl of non-radioactive 1% incadronate aqueous solution was added for dilution.

—Method for Administration and Dose—

The rat abdominal hair was shaved and a round cell (made of acryl, 20 mm in diameter) was fixed on the skin with a medical adhesive. The $^{14}$C-incadronate aqueous solution was poured into the cell (10 mg/kg) and capped to prevent the solution from leaking. During the test, the rat was fixed dorsally under urethane anesthesia.

—Measurement of Radioactivity—

Bone tissue specimens were burnt in a tissue combustion equipment and the radioactivity was counted by a scintillation counter.

Experimental Results

The experimental results are shown in TABLE 1.

TABLE 1

|  | 24 Hours after Percutaneous Administration |
|---|---|
| Concentration in the humerus ($\mu g/g$) | 48.3 + 10.8 |
| Concentration in the costa ($\mu g/g$) | 28.3 + 6.1 |

—Discussions—

As is clear from the foregoing results, incadronate rapidly moved onto the bone by percutaneous route and shows very high concentration in the bone tissues in 24 hours after the administration.

Experiment 2

In Vitro Skin Permeation Test

[Test Method]

In Wistar male rat (7 weeks old) the abdominal hair was shaved and the skin at that area was taken in a diameter of 2 cm. The skin was mounted in a two-chamber diffusion cell. A test drug solution was infused into the donor side and into the acceptor side an isotonic phosphate buffer (pH 7.4) was infused. Samples were collected from the acceptor side with passage of time. The drug content in the samples collected was quantitatively determined by high performance liquid chromatography, and the accumulated permeation amount per unit area was calculated. Comparison was made using as a positive control the skin, from which the stratum corneum having the barrier function in percutaneous permeation was removed (stripped skin).

Formulation Example Nos. 1 through 12

In solution formulation Nos. 1 through 12, the compounding components and amounts are shown in TABLES 2 and 3.

Using 10 parts of crotamiton and 5 parts of surfactant polyoxyethylene sorbitan monooleate having HLB 15 in the case of O/W emulsion, and likewise using 84 parts of crotamiton and 5 parts of sorbitan monooleate having HLB 4.3 in the case of W/O emulsion, 84 parts and 10 parts of purified water were added to 1 part of incadronate, respectively, for emulsification to prepare the O/W and W/O emulsions.

TABLE 2

| Formulation Example No. | 1 | 2 | 3 | 4 | 5 | 6 | 7 | 8 |
|---|---|---|---|---|---|---|---|---|
| Incadronate | 1 | 1 | 1 | 1 | 1 | 1 | 1 | 1 |
| Water | 99 | 64 | 86 | 96 | 89 | — | — | — |
| Ethanol | — | 30 | 10 | — | 10 | — | — | — |
| l-Menthol | — | 5 | 3 | 3 | — | — | — | — |
| Britton-Robinson Buffer (pH 3) | — | — | — | — | — | 99 | — | — |
| Britton-Robinson Buffer (pH 6) | — | — | — | — | — | — | 99 | — |

TABLE 2-continued

| Formulation Example No. | 1 | 2 | 3 | 4 | 5 | 6 | 7 | 8 |
|---|---|---|---|---|---|---|---|---|
| Britton-Robinson Buffer (pH 9) | — | — | — | — | — | — | — | 99 |

TABLE 3

| | Formulation Example No. | | | |
|---|---|---|---|---|
| | 9 | 10 | 11 | 12 |
| Incadronate | 1 | 1 | 1 | 1 |
| Water | 94 | — | — | — |
| Urea | 5 | — | — | — |
| O/W Emulsion | — | 99 | — | — |
| W/O Emulsion | — | — | 99 | — |
| Liquid paraffin | — | — | — | 99 |

Experimental Results

The skin permeation test results described above are shown in TABLE 4.

TABLE 4

| Formulation Example No. | Accumulated Permeation Amount for 8 Hours ($\mu g/cm^2$) |
|---|---|
| 1 (stripped skin) | 1653.9 + 106.6 |
| 1 (intact skin) | 461.4 + 61.7 |
| 2 (intact skin) | 954.5 + 243.7 |
| 3 (intact skin) | 971.5 + 122.9 |
| 4 (intact skin) | 894.8 + 123.9 |
| 5 (intact skin) | 964.3 + 75.9 |
| 6 (intact skin) | 749.4 + 101.1 |
| 7 (intact skin) | 568.7 + 43.7 |
| 8 (intact skin) | 510.7 + 63.7 |
| 9 (intact skin) | 892.8 + 144.6 |
| 10 (intact skin) | 624.8 + 157.0 |
| 11 (intact skin) | 1004.5 + 131.0 |
| 12 (intact skin) | 1536.1 + 92.3 |

[Discussions]

As is evident from the experimental results described above, it was demonstrated that the stratum corneum of skin functions as a barrier for drug permeation in the percutaneous preparation of 1% incadronate aqueous solution; in the formulations added with 30% ethanol+5% l-menthol, 10% ethanol+3% l-menthol, 3% l-menthol and 5% urea, the percutaneous permeation promoting effect by about twice was shown in the system with any percutaneous permeation enhancer, when compared to the 1% incadronate aqueous solution; a tendency to increase the percutaneous permeation amount was noted as the liquid property of the formulations was declined toward the acidic property; the W/O emulsions showed significantly superior percutaneous permeation promoting effects than the O/W emulsions; in the suspension-type formulations using the suspension-type bases such as liquid paraffin, etc., the formulations showed the percutaneous permeability surprisingly far superior to the system added with the percutaneous permeation enhancers or to the W/O emulsion system, which was comparable to the stripped skin.

Experiment 3

In Vitro Skin Permeation Test

[Test Method]

In a manner similar to EXPERIMENT 2, the abdominal hair of Wistar male rat (7 weeks old) was shaved and the skin at that area was taken in a diameter of 2 cm. The skin was mounted in a two-chamber diffusion cell. The percutaneous preparations of EXAMPLE 3 described above, COMPARATIVE EXAMPLE 1 described below and CONTROL 1 described below as well as EXAMPLE 4 described above, COMPARATIVE EXAMPLE 2 described below and CONTROL 2 described below A were infused into the donor side and into the acceptor side an isotonic phosphate buffer (pH 7.4) was infused. Samples were collected from the acceptor side with passage of time. The drug content in the samples collected was quantitatively determined by high performance liquid chromatography, and the accumulated permeation amount per unit area was calculated.

Comparative Example 1

Plaster Formulation (Tape Preparation, Incadronate and Decyl Methyl Sulfoxide)

A 20% aqueous solution containing 2.0 parts of incadronate as the effective ingredient, 5.0 parts of decyl methyl sulfoxide, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 10.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Control 1

Plaster Formulation (Tape Preparation, Incadronate)

A 20% aqueous solution containing 2.0 parts of incadronate as the effective ingredient, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 15.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Comparative Example 2

Plaster Formulation (Tape Preparation, Minodronic Acid and Decyl Methyl Sulfoxide)

A 20% aqueous solution containing 2.0 parts of minodronic acid as the effective ingredient, 5.0 parts of decyl methyl sulfoxide, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 10.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Control 2

Plaster Formulation (Tape Preparation, Minodronic Acid)

A 20% aqueous solution containing 2.0 parts of minodronic acid as the effective ingredient, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 15.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Experimental Results

In the results of the skin permeation test in vitro described above, the accumulated permeation amount for 8 hours ($\mu g/cm^2$) are shown in TABLE 5.

TABLE 5

| EXAMPLE No. | Accumulated Permeation Amount for 8 Hours ($\mu g/cm^2$) |
|---|---|
| EXAMPLE 3 (tape preparation: incadronate, N-methyl-2-pyrrolidone) | 20.64 + 2.03 (intact skin) |
| COMPARATIVE EXAMPLE 1 (tape preparation: incadronate, decyl methyl sulfoxide) | 11.73 + 0.46 (intact skin) |
| CONTROL 1 (tape preparation: incadronate, no amphiphilic solubilizing auxiliary agent) | 1.24 + 1.21 (intact skin) |
| EXAMPLE 4 (tape preparation: minodronic acid, N-methyl-2-pyrrolidone) | 47.00 + 6.58 (intact skin) |
| COMPARATIVE EXAMPLE 2 (tape preparation: minodronic acid, decyl methyl sulfoxide) | 11.15 + 1.14 (intact skin) |
| CONTROL 2 (tape preparation: minodronic acid, no amphiphilic solubilizing auxiliary agent) | 0.93 + 0.09 (intact skin) |

[Discussions]

As is evident also from the experimental results described above, the percutaneous preparation of the present invention containing the amphiphilic solubilizing auxiliary agent exhibited far superior percutaneous permeability through the preparations, as compared to the plaster formulation system containing decyl methyl sulfoxide known to have the percutaneous permeation promoting effect on the bisphosphonates.

Experiment 4

In Vitro Skin Permeation Test

[Test Method]

In a manner similar to EXPERIMENT 2, the abdominal hair of Wistar male rat (7 weeks old) was shaved and the skin at that area was taken in a diameter of 2 cm. The skin was mounted in a two-chamber diffusion cell. The percutaneous preparations of EXAMPLES 5 through 7 described above as well as EXAMPLE 8 described above, COMPARATIVE EXAMPLE 3 described below and CONTROL 3 described below A were infused into the donor side and into the acceptor side an isotonic phosphate buffer (pH 7.4) was infused. Samples were collected from the acceptor side with passage of time. The drug content in the samples collected was quantitatively determined by high performance liquid chromatography, and the accumulated permeation amount per unit area was calculated. The experimental results in EXAMPLES containing the amphiphilic solubilizing auxiliary agent are shown in TABLE 6 and the experimental results examined on the other drugs are shown in TABLE 7.

Comparative Example 3

Plaster Formulation (Tape Preparation, Alendronate and Decyl Methyl Sulfoxide)

A 20% aqueous solution containing 2.0 parts of alendronate as the effective ingredient, 5.0 parts of decyl methyl sulfoxide, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 10.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Control 3

Plaster Formulation (Tape Preparation, Alendronate)

A 20% aqueous solution containing 2.0 parts of alendronate as the effective ingredient, 2.5 parts of α-monoisostearyl glyceryl ether, 5.0 parts of isopropyl myristate and 1.0 part of sorbitan fatty acid ester were blended. After the blend was added to 40.0 parts of styrene-isoprene-styrene block copolymer, 34.5 parts of terpene resin and 15.0 parts of aliphatic hydrocarbon resin, a sufficient quantity of ethyl acetate was added thereto and the resultant was uniformly mixed to form an adhesive mass. The adhesive mass was uniformly applied onto a releasable film followed by drying with warm air. A backing film was laminated and transferred thereon to provide a tape preparation.

Experimental Results

In the results of the skin permeation test in vitro described above, the accumulated permeation amount for 8 hours (μg/cm$^2$) are as follows.

TABLE 6

| EXAMPLE No. | Accumulated Permeation Amount for 8 Hours (μg/cm$^2$) |
|---|---|
| EXAMPLE 5 (tape preparation: minodronic acid, polyoxyethylene lauryl ether) | 29.96 + 2.90 (intact skin) |
| EXAMPLE 6 (tape preparation: minodronic acid, polyethylene glycol monostearate) | 23.08 + 5.70 (intact skin) |
| EXAMPLE 7 (tape preparation: minodronic acid, methyl ethyl ketone) | 28.31 + 6.18 (intact skin) |

TABLE 7

| EXAMPLE No. | Accumulated Permeation Amount for 8 Hours (μg/cm$^2$) |
|---|---|
| EXAMPLE 8 (tape preparation: alendronate, N-methyl-2-pyrrolidone) | 8.56 + 2.60 (intact skin) |
| COMPARATIVE EXAMPLE 3 (tape preparation: alendronate, decyl methyl sulfoxide) | 2.54 + 0.79 (intact skin) |
| CONTROL 3 (tape preparation: alendronate, no amphiphilic solubilizing auxiliary agent) | 0.18 + 0.08 (intact skin) |

[Discussions]

As is evident also from the experimental results described above, it was demonstrated that various amphiphilic solubilizing auxiliary agents showed an excellent percutaneous permeability; the system using these amphiphilic solubilizing auxiliary agents exhibited a more excellent percutaneous permeability with the same drug than those when decyl methyl sulfoxide was used as a percutaneous permeation enhancer, even in the case of using the other bisphosphonates such as alendronate, etc.; and the percutaneous permeability by the aforesaid preparation using minodronic acid as the effective ingredient (EXAMPLE 4) was superior by several times as compared to the preparation using alendronate as the effective ingredient.

INDUSTRIAL APPLICABILITY

As is clear from the foregoing description, the percutaneous preparation in accordance with the present invention shows an excellent percutaneous permeability. By this excellent characteristic, burdens on the patient are thus reduced as compared to the case where other preparation forms using the bisphosphonic acid derivative as the effective ingredient are administered, so that the patient's compliance is not deteriorated even in the administration over a prolonged period of time. In addition, therapeutic effects can be achieved in a short period of time. Therefore, it becomes possible to provide the preparations with expectation of such excellent effects.

The invention claimed is:

1. A plaster formulation comprising: (a) minodronic acid, or pharmaceutically acceptable salts thereof, at from 0.1 to 5 weight percent (b) 0.05 to 5 parts by weight of a solubilizing agent based on 1 part by weight of the minodronic acid or salt thereof, (c) N-methyl-2-pyrrolidone at from 3 to 8 weight percent, and (d) a styrene-isoprene-styrene block copolymer as an adhesive component.

2. The plaster formulation according to claim 1, wherein the plaster formulation is in the form of a tape.

3. A method for treating diseases associated with accelerated bone resorption or ectopic calcification, comprising administering an effective amount of minodronic acid contained in the plaster formulation according to claim 1 to a patient in need thereof.

* * * * *

UNITED STATES PATENT AND TRADEMARK OFFICE
CERTIFICATE OF CORRECTION

PATENT NO.         : 7,820,197 B2
APPLICATION NO.    : 10/502951
DATED              : October 26, 2010
INVENTOR(S)        : Yasuhiro Tsuji et al.

It is certified that error appears in the above-identified patent and that said Letters Patent is hereby corrected as shown below:

Title page, item (73) Assignee, "Astellas Pharma Inc., Tokyo (JP)" should read --Kyukyu Pharmaceutical Co., Ltd., Tokyo (JP)--.

Signed and Sealed this
Seventh Day of June, 2011

David J. Kappos
*Director of the United States Patent and Trademark Office*